United States Patent [19]

Lu et al.

[11] Patent Number: 5,458,623

[45] Date of Patent: Oct. 17, 1995

[54] AUTOMATIC ATRIAL PACING THRESHOLD DETERMINATION UTILIZING AN EXTERNAL PROGRAMMER AND A SURFACE ELECTROGRAM

[75] Inventors: Richard M. T. Lu, Highlands Ranch; Bruce M. Steinhaus, Parker; Peter A. Crosby, Greenwood Village, all of Colo.

[73] Assignee: Telectronics Pacing Systems, Inc., Englewood, Colo.

[21] Appl. No.: 208,140

[22] Filed: Mar. 4, 1994

[51] Int. Cl.$^6$ .................................................. A61N 1/36
[52] U.S. Cl. .................................................. 607/28; 607/30
[58] Field of Search .......................... 607/11, 13, 25–28, 607/30; 128/702, 704

[56] References Cited

U.S. PATENT DOCUMENTS

| | | | |
|---|---|---|---|
| 3,949,758 | 4/1976 | Jirak | 607/28 |
| 4,674,508 | 6/1987 | DeCote | 607/28 |
| 4,708,142 | 11/1987 | DeCote, Jr. | 607/28 |
| 4,817,605 | 4/1989 | Sholder | 607/28 |
| 4,903,700 | 2/1990 | Whigham et al. | |
| 4,969,462 | 11/1990 | Callaghan et al. | |
| 5,165,405 | 11/1992 | Eckwall | 607/13 |
| 5,172,690 | 12/1992 | Nappholz et al. | |
| 5,184,615 | 2/1993 | Nappholz et al. | 607/14 |
| 5,217,021 | 6/1993 | Steinhaus et al. | 128/702 |
| 5,350,410 | 9/1994 | Kleks et al. | 607/28 |
| 5,391,192 | 2/1995 | Lu et al. | 607/28 |

FOREIGN PATENT DOCUMENTS

| | | | |
|---|---|---|---|
| 0545628 | 6/1993 | European Pat. Off. | 607/25 |

OTHER PUBLICATIONS

Preston et al. "The Automatic Threshold Tracking Pacemaker". Medical Instrumentation, vol. 8, No. 6 Nov.–Dec. 1974 pp. 322–325.

*Primary Examiner*—William E. Kamm
*Assistant Examiner*—Jeffrey R. Jastrzab
*Attorney, Agent, or Firm*—Gottlieb, Rackman & Reisman

[57] ABSTRACT

A clinical programming system for use with an implanted cardiac pacemaker to automatically determine the minimum pacing energy which is necessary to evoke an atrial depolarization. The system utilizes a series of pacing pulses of progressively decreasing energies to stimulate the atrium, and detects an evoked response during the AV delay interval that follows each pulse. Initial P-wave intervals are subjected to morphological analysis to generate a P-wave template. Subsequent intervals are similarly analyzed and the results compared with the template. The absence of similarity with the template indicates the loss of atrial capture and that the minimum pacing energy has been reached.

17 Claims, 2 Drawing Sheets

AUTOMATIC ATRIAL PACING THRESHOLD DETERMINATION UTILIZING AN EXTERNAL PROGRAMMER AND A SURFACE ELECTROGRAM

FIELD OF THE INVENTION

This invention relates to implantable pulse generators or other medical devices, including tachycardia reversion devices and defibrillators, and more particularly to determining the minimum pacing energy to "capture" the atrial chambers of a patient's heart, i.e., to cause an atrial contraction.

BACKGROUND OF THE INVENTION

The atrial or ventricular pacing threshold is the minimum pulse energy (usually expressed as a voltage of a fixed width pulse) required to stimulate the muscle cells of the atria or ventricles to depolarize, i.e., to contract.

Pacing thresholds must be determined when the pacemaker, or other therapeutic pulse generator, is first implanted in the patient, and during subsequent follow-up examinations, to ensure that reliable "capture" is obtained while expending minimum energy. This is important since the pacemaker is battery powered and has a limited life. A conventional battery, depending on mode of operation, lead impedance, pulse amplitude, pacing rate and pulse width, may have a longevity typically ranging from four to ten years. Pulse amplitude and pulse width (which translate into energy consumed) are important factors in battery life.

Both the atrial and ventricular pacing thresholds must be measured if a dual chamber device is implanted. If a ventricular single-chamber device is implanted, then only the ventricular pacing threshold is required. If an atrial single-chamber device is implanted, then only the atrial pacing threshold is required. After a pacing threshold is measured, an appropriate pacing energy is chosen and programmed for the implanted pulse generator. The pacing energy is conventionally chosen to be two or three times the measured threshold so as to allow a safety margin for reliable capture.

Thresholds are measured at the time of implant with a pacing system analyzer when direct electrical access to the leads is possible. After implant, when the leads are not accessible, another method must be used. Conventionally, the threshold test is done with the aid of a programmer, which communicates with the implanted pulse generator via a telemetric link, at the same time that the patient's surface electrocardiogram (ECG) is viewed. Conventionally, either the atrial or ventricular threshold test starts from the previously programmed pulse amplitude and pulse width. The test is performed by automatically and progressively decreasing the pacing pulse amplitude by a fixed percent (e.g., 6%) on each test pace. The percent of decrease varies with the impedance of the lead involved. The pacing rate during the threshold test is set at a rate just above the patient's intrinsic rate to ensure that the pacing pulses will capture the heart.

When an atrial threshold is being measured, the amplitude of each decreased amplitude pulse can be annotated on the surface ECG trace. The amplitude of the last pulse to capture the heart represents the "pacing threshold." All pulses are delivered at the last programmed pulse width and pacing polarity. Unless halted manually, the test continues until either the pulse amplitude fails to a minimum predetermined voltage, or a fixed number of decreased amplitude pulses have been delivered.

The operator visually decides from the surface ECG when a loss of capture occurs, and thereupon manually terminates the test. The programmer displays the amplitude of the next-to-last pacing pulse before the termination of the test. If the test was not terminated immediately after that pulse which lost capture, the displayed amplitude will not be the true pacing pulse threshold. Therefore, the pacing pulse threshold must be confirmed by the operator by visual examination of the surface ECG. If the ECG trace is on paper, that portion of the ECG where a loss of capture occurred can be examined. If the ECG provides a trace into only a limited window of storage, then that portion of interest in the ECG may or may not be available, and the test may have to be done again. Thus, the conventional test procedure may be very time consuming. Pacing pulse thresholds also may not be determined appropriately due to operator error and this may have safety consequences for the patient.

In U.S. Pat. No. 4,969,462, issued Nov. 13, 1990 to F. J. Callaghan et al., for "Pacemaker With Improved Automatic Output Regulation", there is disclosed a threshold search by an implantable pacemaker which determines the pacing threshold by sensing the evoked potentials which follow the pacing stimuli and automatically sets the values of pacing energy accordingly. The pacing pulse is delivered between the tip electrode located inside the heart and the case of the pacemaker which is located under the skin on the patient. Sensing for evoked potentials is performed between the ring electrode located in the heart and the case. But in many patients only a unipolar lead, one with a tip electrode but no ring electrode, is available, and therefore pacing and sensing must be done through the same tip and case electrodes. In such a case, measurement of the capture threshold may not be feasible, because the pacing pulse induces potentials in the immediate area of the heart which are very much greater than those resulting from a heartbeat. Until the charges resulting from the pacing pulse dissipate sufficiently, reliable sensing is impossible.

To permit sensing with the same electrodes which are used for pacing, a triphasic stimulation waveform has been described by Whigham et al. in U.S. Pat. No. 4,903,700, issued Feb. 27, 1990, for "Pacing Pulse Compensation". Here the first and third phases of the pacing pulse are of one polarity and the second phase is of the other polarity, so that the net charge to the heart muscle is zero. This allows the same electrode which conducted the pacing pulse to sense the evoked potential. Due to the different surface treatments of pacing electrodes, the procedures described by Nappholz et al. in U.S. Pat. No. 5,172,690, issued Dec. 22, 1992 for "Automatic Stimulus Artifact Reduction For Accurate Analysis of the Heart's Stimulated Response", are advantageously incorporated to optimally adjust the triphasic waveform to reduce the stimulus polarization artifact. However, optimal triphasic waveforms may still be difficult to obtain with electrodes which have very high polarization characteristics.

Moreover, when pacing threshold searches are done routinely by the pacemaker, as described by Callaghan et al. and Nappholz et al., they may unnecessarily consume energy and shorten the life of the battery of the pacemaker due to the energy required to run the threshold searches. This is especially true today with the availability of drug-eluting leads which provide low and stable pacing thresholds.

SUMMARY OF THE INVENTION

Following an atrial pacing pulse, the surface ECG is obtained during the atrioventricular delay interval. A digital filter and other digital signal processing techniques are used to remove baseline offset and noise from the surface ECG. P-waves, albeit initially distorted by the respective atrial pacing pulses, evoked by the first two pacing pulses of highest energy are used to generate a template for the morphological analysis of the P-waves from subsequent pacing pulses to determine capture or lack of capture. If the morphology of the surface ECG obtained during the atrioventricular delay interval following a subsequent atrial pacing pulse is not similar to the morphology of the template, indicating the absence of an evoked P-wave, that pulse is classified as a non-capture pulse. After X out of Y, e.g., 2 out of 5, pulses are classified as non-capture, the threshold procedure is terminated automatically and the energy of the last capture pulse is displayed as the atrial pacing pulse threshold.

To avoid occurrences of competition or fusion beats, or both, pacing is at a faster than normal rate, in the DDD mode instead of the conventional DOO mode. The atrioventricular delay of the pacemaker is programmed to a default value such as 200 ms to allow for ventricular support pacing.

The method of the invention can also be implemented by telemetering out of the pacemaker the intracardiac electrogram signal for processing externally. Similarly, the processing can be completely internal to the implanted device.

DESCRIPTION OF THE DRAWINGS

Further features and advantages of this invention will become apparent upon consideration of the following detailed description in conjunction with the drawing, in which.

DESCRIPTION OF THE INVENTION

Figure 1:
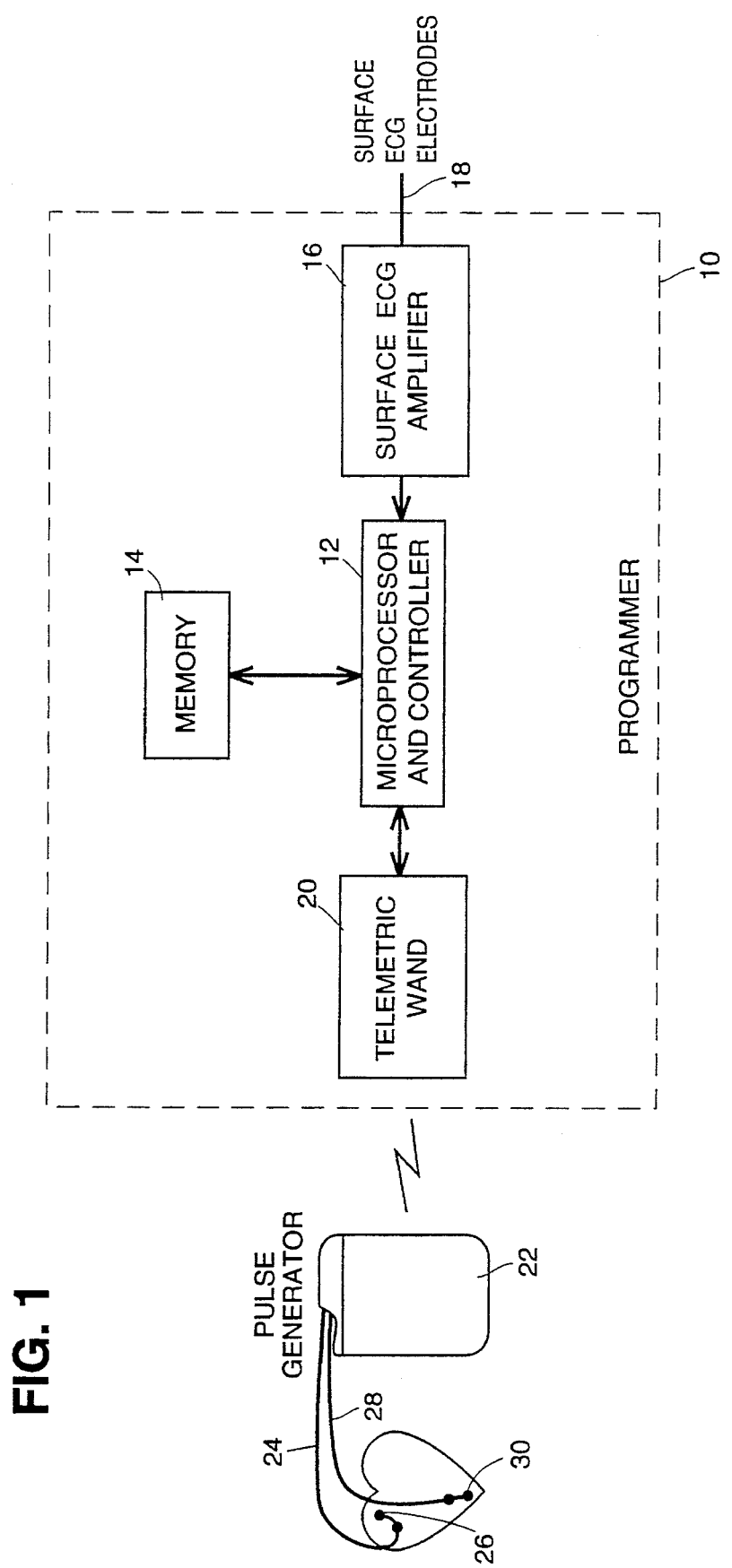
FIG. 1 is a block diagram of the hardware system of the invention including a programmer and an implanted pulse generator.

The hardware system shown in FIG. 1 comprises a programmer 10, which includes a microprocessor and controller 12, a memory 14, a surface electroeardiographic amplifier 16 having a patient cable 18 with surface ECG electrodes (not shown), and a telemetric wand 20. A pulse generator 22 (pacemaker) is implanted in the patient and is here shown as having an atrial lead 24 with an electrode 26 located adjacent to the muscle wall of the right atrium, and a ventricular lead 28 with an electrode 30 located adjacent to the muscle wall of the right ventricle. An exemplary programmer is the 9600 Network Programmer, manufactured by Telectronics Pacing Systems, Inc., which is a combined programmer/ECG monitor and recorder and has several replaceable memory cassettes which contain the operating software and data storage memory required for different pacemakers. An exemplary pulse generator is the META DDDR Model 1254 dual chamber, rate responsive, multiprogrammable, cardiac pulse generator with telemetry and a range of functions which includes fourteen pacing modes. An exemplary atrial lead is a Telectronics Accufix Model 330-801.

The innovative test procedure is initiated by pressing an appropriate key on the programmer to cause a command, via a telemetric link which includes the programmer wand 20 and a telemetry transceiver in the pulse generator, to be issued to the pulse generator to deliver a test pacing pulse sequence to the heart, at a pacing rate which is usually higher than the programmed standby rate (e.g., 100 pulses per minute), in an inhibition mode, which is DDD for an atrial test. The atrial threshold test is performed by progressively decreasing the amplitudes of successive atrial pacing pulses in the sequence by either a certain percentage (e.g., 6%) or a certain voltage (e.g., 0.2 v) for each pulse. [Alternatively, the pulse width may be progressively reduced, or a combination of amplitude and width may be reduced.] Following the delivery of each pacing pulse, main timing event signals are transmitted telemetrically by the pulse generator to the programmer to trigger capture classification.

Figure 2:
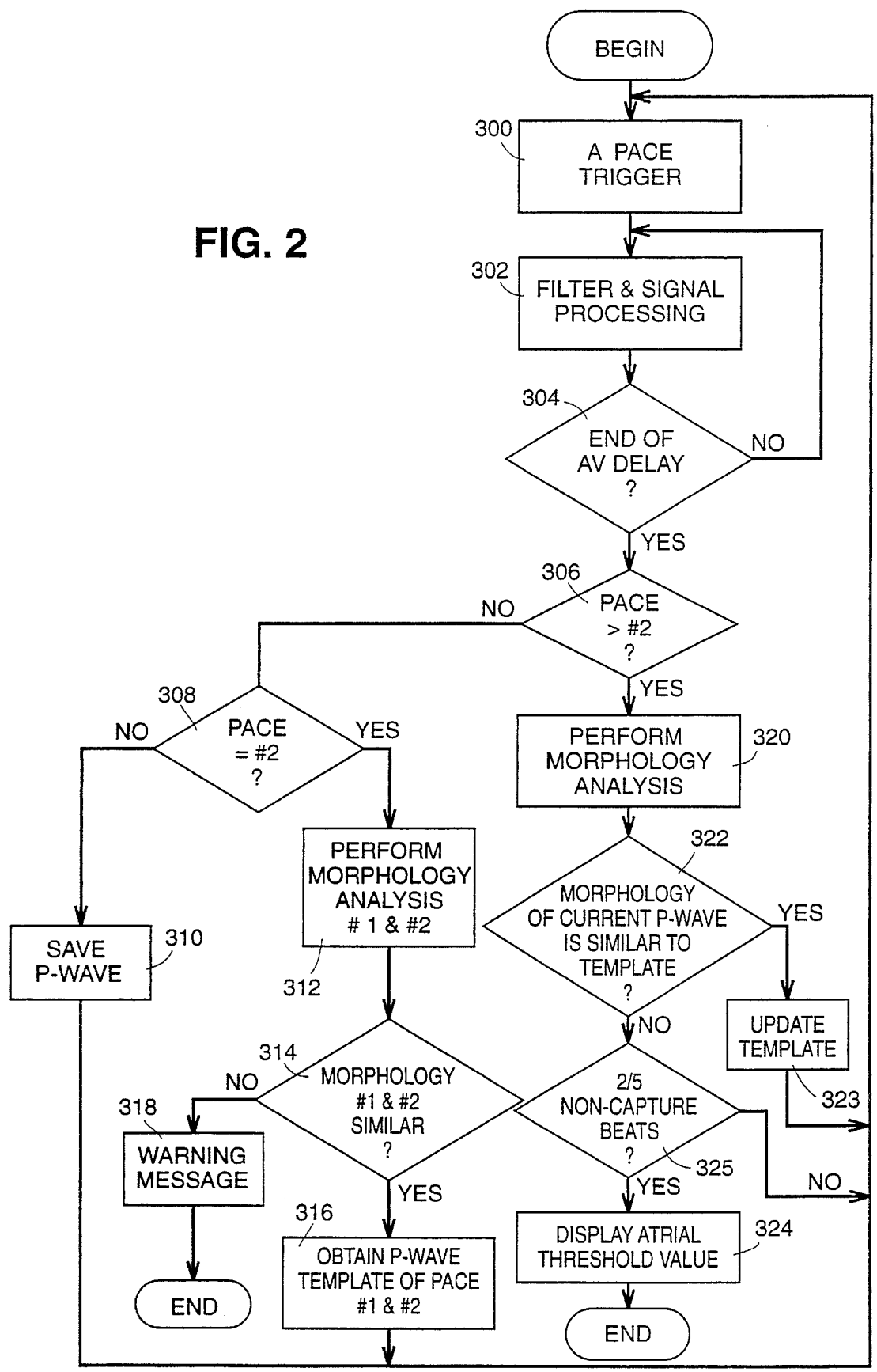
FIG. 2 is a flow chart of the method utilized by the system of FIG. 1 to automatically determine the atrial threshold value for the atrium utilizing morphology analysis.

FIG. 2 shows the flow diagram for determining the atrial capture threshold utilizing a system of P-wave pattern recognition.

The use of templates for morphological analysis is well known, and is taught, for example, in U.S. Pat. No. 5,217,021, issued Jun. 8, 1993 to B. M. Steinhaus et al., for "Detection Of Cardiac Arrhythmias Using Correlation Of Cardiac Electrical Signals And Temporal Data Compression", and in U.S. Patent Application Ser. No. 07/865,320, filed Apr. 9, 1992, by B. M. Steinhaus et al., for "Detection Of Cardiac Arrhythmia Using Temporal Matching By Signature Analysis", which are hereby incorporated by reference.

The A-pace trigger in step 300 enables the surface electrocardiogram to be processed by a digital filter and signal processing block in step 302, which includes, e.g., a 0.8-Hz high pass filter, digital line-frequency notch filters, etc., used to remove baseline offset and noise from the surface ECG signal. After the end of the programmed A-V delay interval determined at step 304 of, for example, 200 ms, the system checks where in the overall A-pace trigger sequence the current pulse lies. If at step 306 it is determined that the pulse is the first or second, and in step 308 it is determined that the pulse is the first, then the P-wave is stored at step 310, and the system waits for the next pulse. On the next A-pace trigger, the tests at steps 304, 306 and 308 cycle the processing to step 312 where morphology analysis is performed on both the stored initial P-wave and the second P-wave. If at step 314 these two P-waves have a correlation coefficient of at least 0.8 when correlation waveform analysis is used, then they are considered similar, the P-wave template, which is the sample-by-sample average of the first two captured P-waves, is stored at step 316, and the system waits for the next A-pace trigger. But if these first and second P-waves are not similar, then in step 318 a warning message is displayed on the programmer and the procedure ends. Also, both P-waves must represent evoked potentials, e.g., by having amplitudes which exceed a predetermined value; otherwise two similar waveforms following atrial pacing pulses, while similar, might not be capture P-waves.

If a P-wave template has been stored, then on the third and subsequent A-pace triggers morphology analysis takes place in step 320, and in step 322 it is determined whether the current P-wave is similar, e.g., has a correlation coefficient of at least 0.8 when correlation waveform analysis is used, to the stored template which was based on the first and second P-waves. If the current P-wave is similar, then the template is updated in step 323 and the system awaits the next A-pace trigger. If the current P-wave is not similar and there are X out of the last Y (e.g., 2 out of 5) P-waves classified as not similar to the template, as determined in step 325 (i.e., non-capture beats), then in step 324 there is displayed the amplitude of the last pulse which was similar and, therefore, was the last A-pace to obtain capture, and the procedure ends. (In general, the first non-similarity determination is an indication that the minimum energy may have been reached.)

If there is an intrinsic R-wave during one or both of the first two cycles within the programmed AV delay, then the template width for the entire test is shortened to exclude R-waves. Otherwise, the template width may be as long as the programmed AV delay. The reason for this is that R-waves should not interfere with the P-wave morphology analysis.

As described above, the initial template for P-wave morphology analysis is determined by operating only on the first two capture P-waves. If desired, the template may be updated following every capture P-wave by forming a composite of all previous capture P-waves.

It is also believed that the best possible P-wave signal, when using a surface ECG, is that derived from a P lead which one electrode located directly above $V_1$ in the first interCostal space, and the second electrode located approximately three inches below $V_4$ (where $V_1$ and $V_4$ are standard ECG electrode locations).

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What is claimed is:

1. A method of determining a minimum energy of a pacing pulse necessary to evoke an atrial depolarization response in the heart of a patient, comprising the steps of:
   (a) generating a series of test atrial pacing pulses of sequentially decreasing energy;
   obtaining a surface electrogram representing evoked atrial responses to said atrial pacing pulses; each evoked atrial response being characterized by a corresponding morphology;
   (c) performing morphological analyses on an initial plurality of evoked atrial responses and generating a morphology template of the results of said analyses;
   (d) comparing the morphology of each subsequent evoked test atrial response with said template and, if they are similar, then repeating steps (b) and (c) for the next evoked test atrial response; and
   (e) concluding that a minimum energy may have been determined when the morphology of an evoked test atrial response is not similar to said template.

2. A method according to claim 1 wherein said step (e) further comprises performing correlation waveform analysis on said template and a compared morphology and considering them to be similar if they have a correlation coefficient of at least 0.8.

3. A method according to claim 1 further including the step of adjusting said template to have a width that does not include ventricular beats.

4. A method according to claim 1 wherein during said step (e) it is concluded that a minimum energy has been determined when X out of the last Y evoked atrial responses are not similar to said template.

5. A method according to claim 1 further including the step of changing said template after the most recent similar evoked atrial response so that it is a composite of all preceding similar evoked atrial responses including the most recent.

6. A method of determining a minimum energy of a pacing pulse necessary to evoke an atrial depolarization response in the heart of a patient comprising the steps of:
   (a) generating a first test atrial pacing pulse of predetermined energy;
   (b) obtaining a surface electrogram representing a first evoked atrial response to said first test atrial pacing pulse;
   (c) storing the evoked atrial response of said first test atrial pacing pulse;
   (d) generating a second test atrial pacing pulse of predetermined energy;
   (e) obtaining another surface electrogram representing a second evoked atrial response to said second test atrial pacing pulse;
   (f) performing morphological analysis of the evoked atrial responses which followed said first and second test atrial pacing pulses;
   (g) determining whether the morphological analysis results of the first and second evoked atrial responses are similar and, if similar, then deriving and storing a P-wave template of the combined morphological analysis results;
   (h) generating a series of test atrial pulses of sequentially decreasing energy;
   (i) comparing a morphology of each atrial response evoked by a test pulse in said series with said template and, if they are similar, then repeating steps g and h for the next evoked test atrial response; and
   (j) concluding that a minimum energy has been determined when the morphology of an evoked test atrial response is not similar to said template.

7. A method according to claim 6 wherein said performing step further comprises representing said evoked atrial responses in telemetered intracardiac signals and performing said morphological analysis external to the patient.

8. A method according to claim 6 wherein said step (j) further comprises performing correlation waveform analysis on said template and a compared morphology and considering them to be similar if they have a correlation coefficient of at least 0.8.

9. A method according to claim 6 further including the step of adjusting said template to have a width that does not include ventricular beats.

10. A method according to claim 6 wherein said step (j) further comprises concluding that a minimum energy has been determined when X out of the last Y evoked atrial responses are not similar to said template.

11. A method according to claim 6 further comprising the step of changing said template after the most recent similar evoked atrial response so that it is a composite of all preceding similar evoked atrial responses including the most recent.

12. Apparatus for determining a minimum energy of a pacing pulse necessary to evoke an atrial depolarization response in the heart of a patient, comprising:
   (a) means for generating a series of test atrial pacing pulses of sequentially decreasing energy;
   (b) means for obtaining a surface electrogram representing evoked atrial responses to said test atrial pacing pulses; and
   (c) analysis means for
      (i) performing morphological analyses on an initial plurality of evoked test atrial responses and generating a morphology template of the results of said analyses, (ii) comparing a morphology of each subsequent evoked test atrial response with said template and, if they are similar, then performing morphological analyses for the next evoked test atrial response, and (iii) concluding that said minimum energy may have been determined when the morphology of an evoked test atrial response is not similar to said template.

13. Apparatus according to claim 12 wherein said pulse generating means is adapted to be implanted and further includes means for telemetering out intracardiac signals, and said analysis means is external to said patient and operates on said telemetered intracardiac signals.

14. Apparatus according to claim 12 wherein said analysis means includes means for comparing said template and a compared morphology and wherein said template and said compared morphology are considered to be similar if they have a correlation coefficient of at least 0.8 when correlation waveform analysis is used.

15. Apparatus according to claim 12 wherein said analysis means adjusts said template to have a width that does not include ventricular beats.

16. Apparatus according to claim 12 wherein said analysis means concludes that a minimum energy has been determined when X out of the last Y evoked atrial responses are not similar to said template.

17. Apparatus according to claim 12 wherein said analysis means changes said template after the most recent similar evoked atrial response so that it is a composite of all preceding similar evoked atrial responses including the most recent.

* * * * *